US010213759B2

(12) United States Patent
Byström et al.

(10) Patent No.: US 10,213,759 B2
(45) Date of Patent: Feb. 26, 2019

(54) AUXILIARY REACTOR FOR BIOLOGICAL OR CHEMICAL TRANSFORMATION

(71) Applicant: SPINCHEM AB, Umeå (SE)

(72) Inventors: Emil Byström, Umeå (SE); Henrik Scherman, Umeå (SE); Lars Eklund, Umeå (SE); Knut Irgum, Bullmark (SE)

(73) Assignee: SPINCHEM AB, Umea (SE)

( * ) Notice: Subject to any disclaimer, the term of this patent is extended or adjusted under 35 U.S.C. 154(b) by 223 days.

(21) Appl. No.: 15/029,024

(22) PCT Filed: Feb. 20, 2014

(86) PCT No.: PCT/SE2014/050208
§ 371 (c)(1),
(2) Date: Apr. 13, 2016

(87) PCT Pub. No.: WO2015/126291
PCT Pub. Date: Aug. 27, 2015

(65) Prior Publication Data
US 2016/0256843 A1  Sep. 8, 2016

(51) Int. Cl.
*B01J 19/18* (2006.01)
*B01J 8/02* (2006.01)
(Continued)

(52) U.S. Cl.
CPC ............. *B01J 8/0278* (2013.01); *B01F 7/163* (2013.01); *B01F 7/1625* (2013.01); *B01F 7/32* (2013.01); *B01F 13/1027* (2013.01); *B01J 4/004* (2013.01); *B01J 8/0015* (2013.01); *B01J 8/04* (2013.01); *B01J 8/085* (2013.01); *B01J 8/10* (2013.01); *B01J 8/20* (2013.01);
(Continued)

(58) Field of Classification Search
CPC .............................. B01J 19/1837; B01J 8/382
USPC .................................. 422/132, 211, 209, 603
See application file for complete search history.

(56) References Cited

U.S. PATENT DOCUMENTS 2,935,495 A  5/1960  Kennedy
4,172,877 A  10/1979  Schwaig
(Continued)

FOREIGN PATENT DOCUMENTS

WO  WO-2008137846 A2  11/2008
WO  WO-2011098570 A2   8/2011

OTHER PUBLICATIONS

International Search Report dated Nov. 11, 2014 for PCT Application No. PCT/SE2014/050208.
(Continued)

*Primary Examiner* — Natalia Levkovich
(74) *Attorney, Agent, or Firm* — Moser Taboada

(57) ABSTRACT

The present invention relates to the field of biological and chemical transformation as well as physical and chemical trapping. More specifically, the invention relates to a new reactor arrangement for performing, by means of at least one solid reaction member, biological or chemical transformation, or physical or chemical trapping from or release of agents to, a fluidic medium. The reactor arrangement is comprised of an auxiliary reactor having a transformation device and a main reactor. The invention also provides an auxiliary reactor adapted for being connected to a main reactor, a method of using such a reactor arrangement, as well as a process involving the reactor arrangement.

15 Claims, 10 Drawing Sheets

Figure 1:
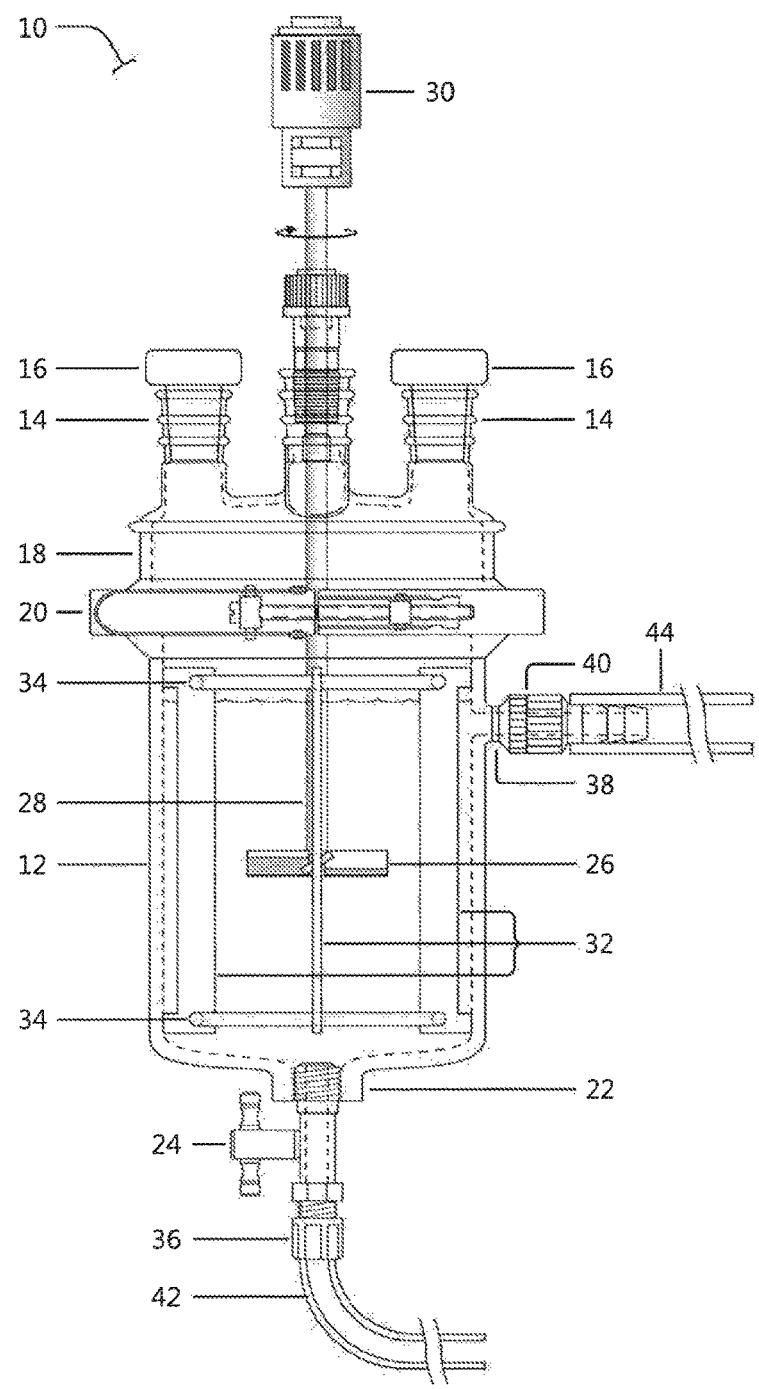

(51) Int. Cl.
| | |
|---|---|
| *C12N 11/00* | (2006.01) |
| *B01F 7/16* | (2006.01) |
| *B01F 7/32* | (2006.01) |
| *B01F 13/10* | (2006.01) |
| *B01J 8/20* | (2006.01) |
| *B01J 19/00* | (2006.01) |
| *B01J 8/04* | (2006.01) |
| *B01J 8/08* | (2006.01) |
| *B01J 8/10* | (2006.01) |
| *B01J 4/00* | (2006.01) |
| *B01J 8/00* | (2006.01) |

(52) U.S. Cl.
CPC ......... *B01J 19/006* (2013.01); *B01J 19/0066* (2013.01); *B01J 19/18* (2013.01); *B01J 19/1806* (2013.01); *B01J 19/1862* (2013.01); *B01J 19/1881* (2013.01); *C12N 11/00* (2013.01); *B01J 2208/00938* (2013.01); *B01J 2208/02* (2013.01); *B01J 2219/00765* (2013.01); *B01J 2219/1943* (2013.01)

(56) References Cited

U.S. PATENT DOCUMENTS

| | | | |
|---|---|---|---|
| 4,683,062 A | 7/1987 | Krovak et al. | |
| 6,245,304 B1* | 6/2001 | Jansen | ............ B01J 8/22 210/321.8 |
| 2012/0209033 A1* | 8/2012 | Hassan | ............ B01F 7/00766 568/850 |

OTHER PUBLICATIONS

Mallin et al., "Efficient Biocatalysis with Immobilized Enzymes or Encapsulated Whole Cell Microorganism by Using the SpinChem Reactor System", Chemcatchem, vol. 5, Issue 12, pp. 3529-3532, Oct. 11, 2013.

Extended European Search Report dated Jul. 17, 2017 for Application No. 14883065.6.

* cited by examiner

Prior art

Figure 9a – 9c
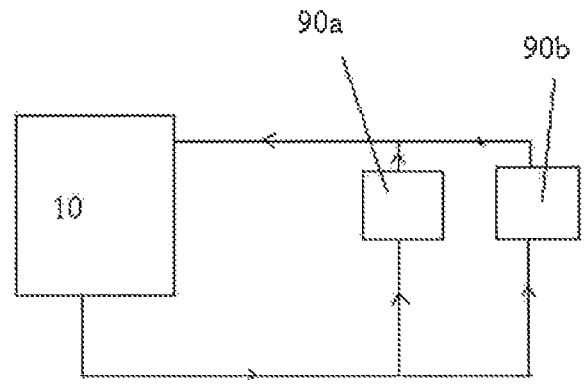
Fig. 9a
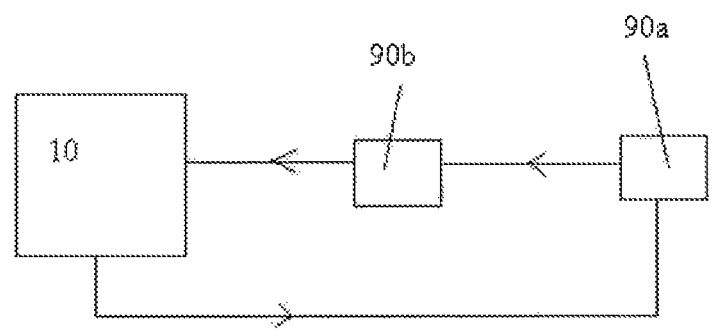
Fig. 9b
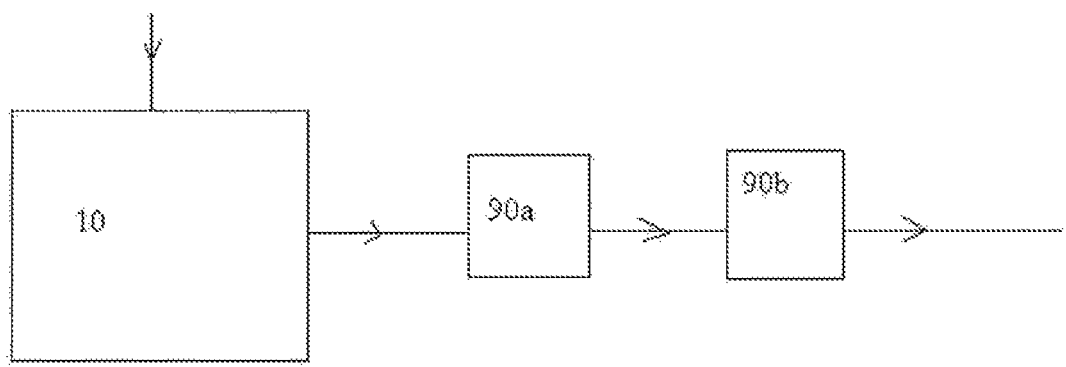
Fig. 9c

Figure 9d – 9f
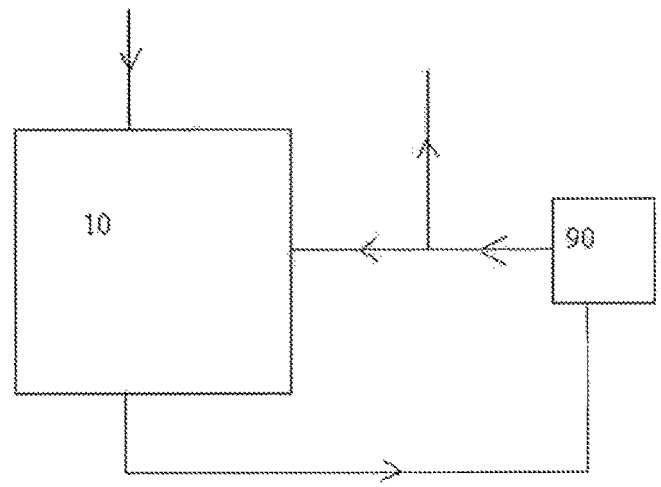
Fig. 9d
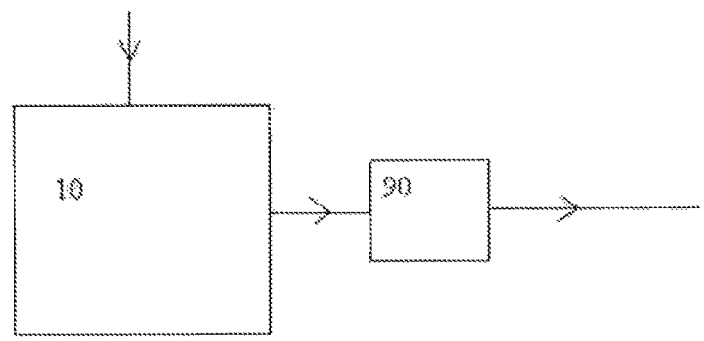
Fig. 9e
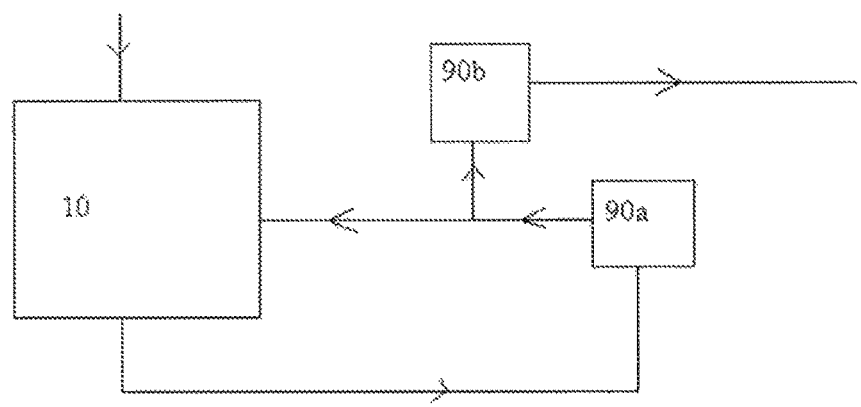
Fig. 9f

AUXILIARY REACTOR FOR BIOLOGICAL OR CHEMICAL TRANSFORMATION

FIELD OF INVENTION

The present invention relates to the field of biological and chemical transformation as well as physical and chemical trapping. More specifically, the invention relates to a new reactor arrangement for performing, by means of at least one solid reaction member, biological or chemical transformation, or physical or chemical trapping from, or release of agents to, a fluidic medium. The reactor arrangement is comprised of an auxiliary reactor having a transformation device and a main reactor. The invention also provides an auxiliary reactor adapted for being connected to a main reactor, a method of using such a reactor arrangement, as well as a process involving the reactor arrangement.

BACKGROUND OF THE INVENTION

Heterogeneous processes in chemistry and biotechnology are unit operations that encompass a solid member (including, but not limited to, immobilized chemical reagents, catalysts, scavengers, reaction supports, trapping sorbents, or immobilized biological materials such as enzymes, or cells or fragments thereof) contacting a fluidic medium carrying reactants or other agents, sample solutes, and/or products of the interactive processing of fluid-conveyed agent(s) with the solid member(s). Most such heterogeneous processes are critically dependent on convective flow of the fluidic medium to establish the necessary mass transfer between the fluidic and solid phases. As a consequence, solid/fluid heterogeneous systems are therefore often operated in a continuous flow through mode, in which case a conventional packed column with a suitable design is often the preferred format for encapsulating the solid member that is to be transited or percolated by the reaction medium. Numerous processes are, however, unfit for continuous processing. This applies in particular to processes where the solid member is a soft and compressible gel which is prone to collapse in a packed column bed, in transformation schemes where sequential addition of agents and/or removal of by-products or desired products are necessary, or where the physical or chemical conditions must otherwise be altered during the course of processing with the solid member. In those cases, a batch-wise processing model is often preferred. Such batch-wise heterogeneous processing can either be done by suspending the solid member directly in the fluid medium as particulate material under agitation, a process that will normally call for a filtration or sedimentation step to separate the phases after the process has been brought to an end. Alternatively, the fluidic medium can be circulated from the batch reactor through a packed reservoir containing the solid member by means of a specially designed flow system comprising pumps and/or valves or the like, in order to accomplish the convective mass transfer needed for the transformation to take place. Such reactors are often quite complicated and must regularly be built on-site and adapted for a specific purpose.

The challenge of establishing efficient convective mass transfer between solid and fluid phases has been addressed in different ways. Some interesting alternatives are disclosed in WO 2011/098570, which relates to devices for performing biological or chemical transformation, or physical or chemical trapping from, or release of agents to, a fluidic medium by means of a solid reaction member. These devices are comprised of a flow distributor having a fluid medium inlet, a fluid medium outlet, at least one confinement where said transformation, trapping, or release of agents is performed, and a means for rotating, rocking, wagging, or oscillating the flow distributor, by which action fluidic medium in which it is submerged is pumped through a bed of solid member contained within the flow distributor.

As a result of this pumping action, use of the devices disclosed in WO 2011/098570 leads to increased convective mass transfer, and accordingly improved performance of most heterogeneous transformation schemes. One of the reasons for these enhanced convective mass transfer properties is the ability of the flow distributor to use a combination of centrifugal force and flow dynamics to draw fluid through the central inlet(s) and discharge it through the peripheral outlets, resulting in a pumping action that predominantly draws fluid from the larger central inlet located at the bottom of the device.

The disclosure of WO 2011/098570 is focused on laboratory scale processes and laboratory scale equipment. However, there are important issues to consider when scaling up a process which are not relevant when working in a laboratory scale. Examples of such issues could be overall cost efficiency and flexibility. Accordingly, there is a need for process equipment capable of providing increased convective mass transfer, and accordingly improved performance of most heterogeneous transformation schemes also in a pilot scale and a large scale.

The present inventors have realized that it would be particularly attractive to have a scheme where an auxiliary reactor can be connected to an existing main reactor, to provide the above-mentioned advantages without having to replace or substantially modify an already existing main reactor.

SUMMARY OF THE INVENTION

In a first aspect, the invention provides an auxiliary reactor for performing, by means of at least one solid reaction member(s), a biological or chemical transformation, or physical or chemical trapping from or release of agents to a fluidic media, said auxiliary reactor being adapted for being connected to a main reactor, said auxiliary reactor comprising a cylindrical reaction vessel having a first end part, a second end part, and an outer wall comprising an outer surface and an inner surface between these parts, in which auxiliary reactor a transformation device has been mounted, said transformation device comprising a flow distributor having an essentially cylindrical shape, a first essentially flat surface, a second essentially flat surface, and a peripheral wall having an essentially circular cross-section, at least one fluid medium inlet located in vicinity of the center of said first and/or second surface, said inlet being adapted for receiving fluid medium and optionally being adapted for receiving initially suspended solid reaction members, at least one fluid medium outlet permeable for said fluid medium but impermeable for solid reaction members, said outlet(s) being located on said peripheral wall, a driving shaft located on said first surface for enabling rotation or oscillation of the flow distributor, and at least one confinement wherein said solid reaction member(s) can be trapped and said transformation is performed; and a means for rotating and/or oscillating the device; wherein said auxiliary reactor further comprises:

a) an inlet connection adapted for being connected to an outlet of said main reactor; and b) an outlet connection adapted for being connected to an inlet of said main reactor.

Transformation devices comprising a flow distributor and means for rotating or oscillating the flow distributor have been described in WO 2011/098570.

As disclosed herein, the term "inlet connection adapted for being connected to an outlet of said main reactor" relates to a conduit for establishing contact between the fluid medium present in the main reactor and the fluid medium present in the auxiliary reactor. Similarly, the term "outlet connection adapted for being connected to an inlet of said main reactor" relates to another conduit for establishing contact between the fluid medium present in a main reactor and the fluid medium present in the auxiliary reactor. Examples of such conduits are a pipe or a hose optionally joined to mechanical connectors fitted to the auxiliary reactor. Such conduits are adapted for connecting to a main reactor, which could optionally be joined by mechanical connectors. In some embodiments a mechanical connector is arranged directly adjacent to an inlet/outlet of the auxiliary reactor. In some embodiments, a hose or a pipe is attached to an inlet/outlet of the auxiliary reactor and a mechanical connector is arranged at the end of the pipe or hose. The skilled person knows how to select suitable connections and connector mechanisms.

In some embodiments, the auxiliary reactor inlet connected to said inlet connection is located at the first end part or at the second end part, and the auxiliary reactor outlet connected to said outlet connection is located in said outer wall adjacent to said flow distributor.

Normally, the pumping effect of a rotating or oscillating flow distributor is sufficient in order to induce and maintain a flow of liquid reaction medium from a main reactor, through the auxiliary reactor and back again. However, in some embodiments, the auxiliary reactor further comprises a pump adapted for pumping a liquid reaction medium from a main reactor through said inlet connection, cylindrical reactor vessel, and outlet connection back to said main reactor.

In some embodiments, said inner surface of the cylindrical reactor vessel comprises means for enhancing the fluidic shear stress in any of the two rotary directions along said inner surface between said first end part and said second end part.

As disclosed herein, the term "means for enhancing the fluidic shear stress" relates to some different types of protrusions from the inner surface capable of causing perturbations in the fluidic media flow close to the inner wall of the reactor vessel that is caused by the rotational movement of the flow distributor. Such means typically has a small volume, and the total volume of such means in a reactor according to the invention typically amounts to less than 10% of the total volume of the reactor vessel. In some embodiments, the total volume of such means amounts to less than 8%, 6%, 5%, 4%, 3% or 2%, respectively, of the total volume of the reactor vessel. Examples of protrusions of semi-elliptical, rectangular, and triangular shape are given in FIG. 6, but the invention is not limited to these specifically exemplified embodiments; instead protrusions of numerous other shapes are conceivable and in varying number and height, that would cause sufficient perturbation of the shear layer to induce a turbulent flow, will fulfill the criteria of a working device according to the invention and a skilled worker should be able to figure out alternative protruding geometries falling within the scope of the invention, based on the examples given in these disclosures.

In some embodiments, said means for enhancing the fluidic shear stress is at least one semi-elliptically-shaped grove in said inner wall extending in a direction from said first end part to said second end part. In one embodiment, the inner wall of the reactor vessel comprises a plurality of such semi-elliptically-shaped groves. In one embodiment, said groves are arranged adjacent to each other. In one embodiment, the depth of said groves amount to 10-50% of the width of the groves.

In some embodiments, the auxiliary reactor comprises 2-30 of said means for enhancing the fluidic shear stress. In other embodiments, the auxiliary reactor comprises 3-30, 4-30, 5-30, 6-30 or 8-25 of said means.

In a second aspect, the invention provides a reactor arrangement for performing, by means of at least one solid reaction member, a biological or chemical transformation, or physical or chemical trapping from, or release of agents to, a fluidic media in a continuous process or in a batch process, wherein said reactor arrangement comprises a main reactor and at least one auxiliary reactor according to the first aspect, wherein the inlet connection of the auxiliary reactor is connected to an outlet of the main reactor.

As disclosed herein, the term "main reactor" relates to a reactor for carrying out typical biological or chemical transformations or physical or chemical trappings. In some embodiments, such a reactor may be a standard reactor for batch-wise chemical synthesis. In some embodiments, the reactor may be a standard reactor for biological transformations, or enzymatic reactions. Such reactors typically comprise outlet and inlet openings that could be used in accordance with the claims. Typically, the main reactor is larger than the auxiliary reactor and in some embodiments, the reactor is substantially larger. In some embodiments, the auxiliary reactor has a volume within the range of 0.1-400 liters, and the main reactor has a volume within the range of 1.0-40000 liters. In some embodiments, the volume of the main reactor is 2-100 times larger than the auxiliary reactor.

In some embodiments, the outlet port of one of the at least one auxiliary reactor is connected to an inlet port of the main reactor.

In some embodiments, the reactor arrangement is adapted for forwarding at least 0-100% of the outgoing flow of fluidic media from an auxiliary reactor of the arrangement to downstream processing. Accordingly, in some embodiments relating to batch processes, the whole flow of fluidic media is returned to the main reactor. In some embodiments relating to continuous processes the whole flow or parts thereof is forwarded to downstream processing. Hence, for example 5%, 10%, 15%, 20%, 25%, 30%, 35%, 40%, 45%, 50%, 55%, 60%, 65%, 70%, 75%, 80%, 85%, 90%, or 95% could be forwarded to downstream processing. As disclosed herein, the term downstream processing relates to process steps carried out after the transformation carried out in the reactor arrangement in order to purify or modify a particular component that has been transformed.

In some embodiments, said main reactor further comprises an agitator for stirring said fluidic media, in certain embodiments assisted by a plurality of baffles, which could be designed as separate entities or indentations in the vessel. Any agitator and baffle set normally used together with a reactor as outlined above may be used.

In some embodiments, the main reactor further comprises an outlet opening fitted with an auxiliary means for state transformation or exchange of matter, or for measurement probes. Examples are a cooler for condensing or freezing out gaseous substances escaping through the outlet opening, or sorbents or fluids for trapping reactants, products, or by-products likewise transported out of the main reactor through said outlet(s). Examples of measurement probes are thermometric or photometric sensor probes, and various electrodes for carrying out electrochemical measurements.

In a third aspect, the invention provides using a reactor arrangement according to the second aspect, in a method for performing, by means of at least one solid reaction member(s), a biological or chemical transformation, or physical or chemical trapping from or release of agents to a fluidic media.

In a fourth aspect, the invention provides a method for performing, by means of at least one solid reaction member(s), a biological or chemical transformation, or physical or chemical trapping from or release of agents to a fluidic media, comprising the steps of:
a) providing a reactor arrangement according to the second aspect;
b) adding at least one solid reaction member to a confinement of said flow distributor;
c) adding a fluidic media to the main reactor and the auxiliary reactor of the reactor arrangement; and
d) activating the means for rotating and/or oscillating the device; whereby the biological or chemical transformation, or physical or chemical trapping from or release of agents to a fluidic media is initiated.

In some embodiments, the method comprises the step of continuous removal a product or by-product formed during the transformation, for instance by a step selected from the group of distillation, extraction, filtration, and adsorption.

In some embodiments, the method comprises the step of trapping inside the flow distributor solid particles that are initially suspended in the fluidic media, or have been produced in situ therein.

In some embodiments, the fluidic media is an aqueous solution containing specific radioactive ions and the flow distributor comprises an organic or inorganic ion exchanger, or other solid materials capable of adsorbing said specific radioactive ions.

DETAILED DESCRIPTION OF THE INVENTION

The above mentioned problems are solved by the invention by providing what is defined by the appended claims and in the summary section above.

In general terms, the present invention provides a reactor combination comprising a main reactor and an auxiliary reactor comprising a transformation device. Typically, the auxiliary reactor is smaller than the main reactor. There are two connections available for communication of fluidic media between the main reactor and the auxiliary reactor in order to enable circulation of fluidic media from the main reactor through the auxiliary reactor and back again to the main reactor. The auxiliary reactor is equipped with a transformation device comprising a flow distributor and a means for rotating or oscillating the flow distributor. The rotation or oscillation of the flow distributor has a pumping effect and is capable of inducing and maintaining a flow of fluidic media from the main reactor through the auxiliary reactor and back again to the main reactor.

Typically, the main reactor is larger than the auxiliary reactor and in some embodiments, the reactor is substantially larger. In some embodiments, the auxiliary reactor has a volume within the range of 0.1-10 liters, and the main reactor has a volume within the range of 1.0-1000 liters. In some embodiments, the volume of the main reactor is 2-100 times larger than the auxiliary reactor.

The present reactor arrangement provides several advantages. A pilot scale or production scale multipurpose batch reactor is large and heavy. Maintenance of such reactors is complicated and laborious. Although a transformation device in accordance with the disclosure of WO 2011/098579 A1 provides important advantages, such as increased convective mass transfer and accordingly improved performance of most heterogeneous transformation schemes, permanent installation of a transformation device is often neither technically nor economically feasible, and maintenance work on a pilot scale or production scale multipurpose batch reactor comprising such a transformation device would be extremely difficult and complicated. Furthermore, it would be very expensive and complicated to de-assemble and re-assemble such a reactor in case it would be desirable to run an occasional batch synthesis without such a transformation device. By using a reactor arrangement according to the present invention, a far more flexible solution is achieved and maintenance is much easier. The transformation device is not installed in the main reactor. Instead, a typically smaller auxiliary reactor is connected to the main reactor. In some embodiments, an existing pilot scale or production scale multipurpose reactor is retrofitted by connecting an auxiliary reactor in accordance with what is specified in the present claims.

BRIEF DESCRIPTION OF THE ENCLOSED FIGURES

Figure 2:
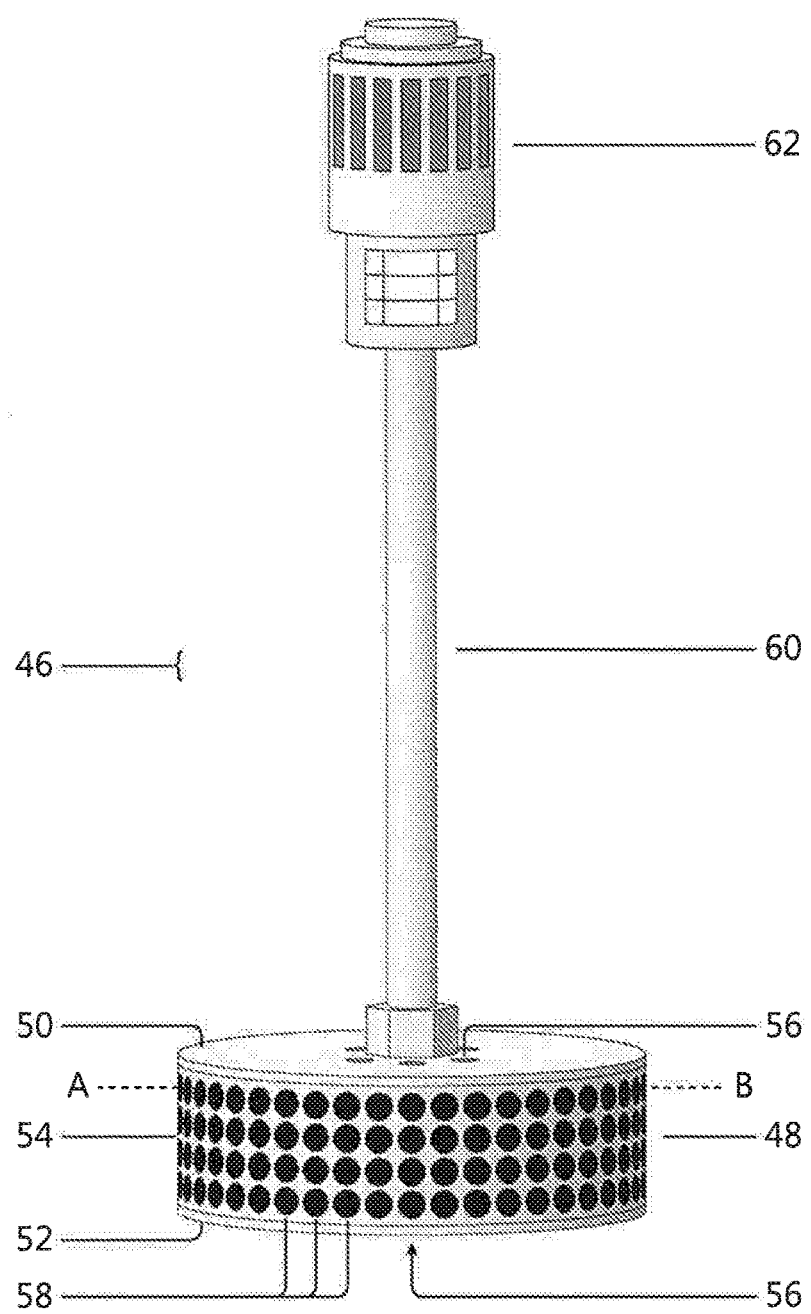

The present invention will now be further disclosed with reference to the enclosed figures, in which:

FIG. 1 presents a side view of a typical main reactor that could be included in a reactor arrangement in accordance with the present invention for performing a biological or chemical transformation, or physical or chemical trapping from, or release of agents to, a fluidic media by means of a solid reaction member;

FIG. 2 shows a side view of an embodiment of a transformation device

Figure 3:
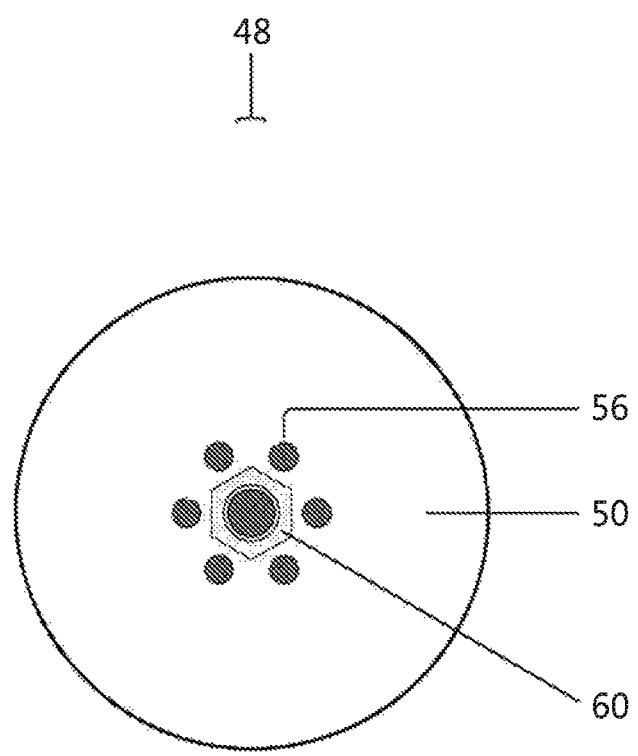
Figure 4:
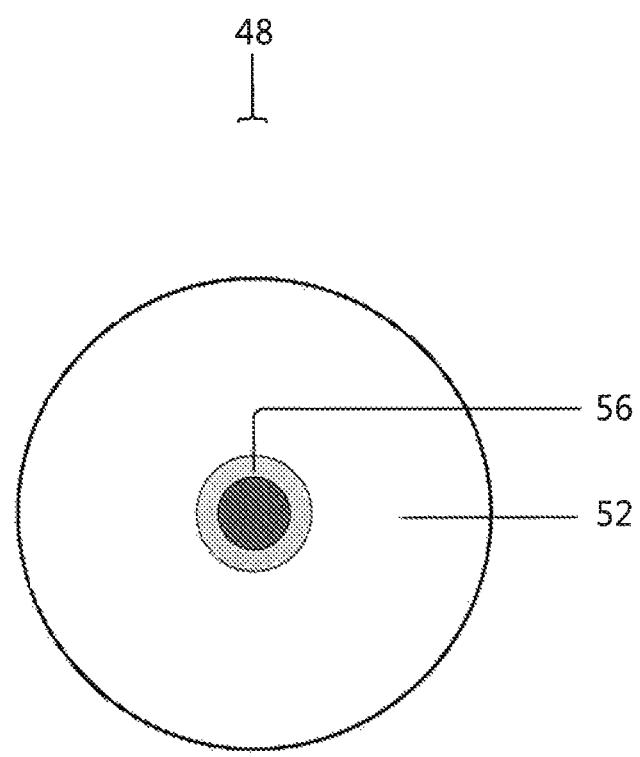
Figure 5:
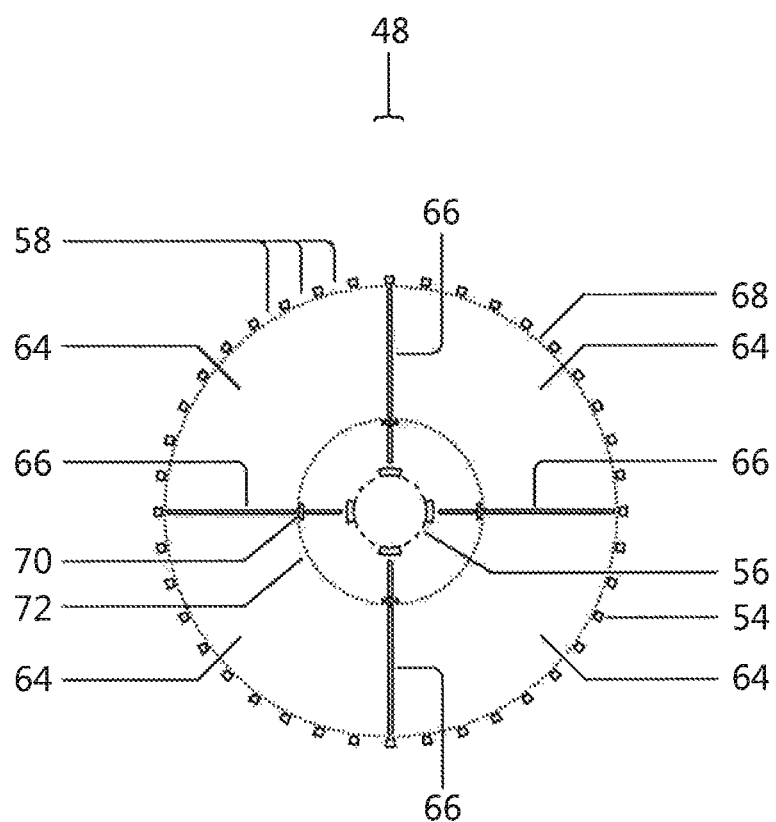

FIG. 3 outlines the second surface of an embodiment of the flow distributor;

FIG. 4 discloses a view of the first surface of an embodiment of the flow distributor of the transformation device in FIG. 2;

FIG. 5 shows a horizontal cross-sectional view from below along the line A-B of the embodiment of a transformation device shown in FIG. 2.

Figure 6:
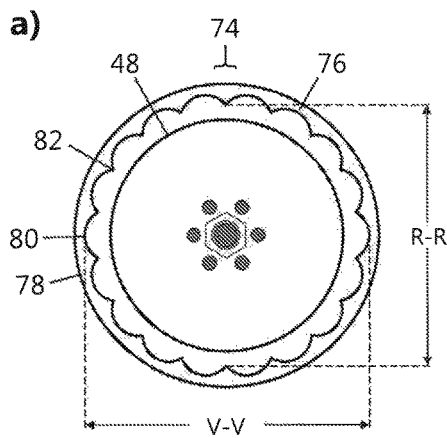
Figure 6:
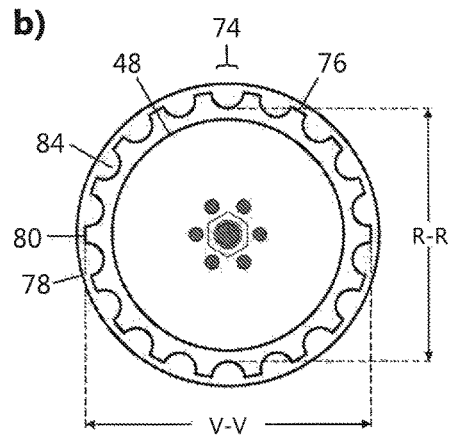
Figure 6:
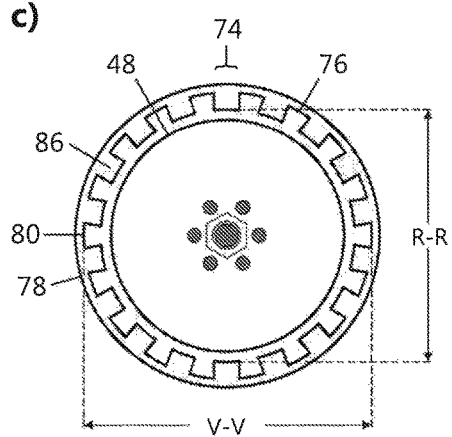
Figure 6:
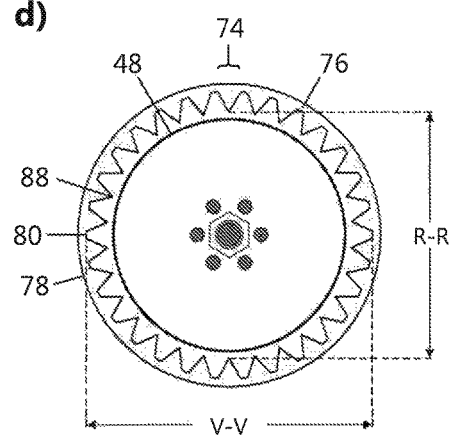
Figure 7:
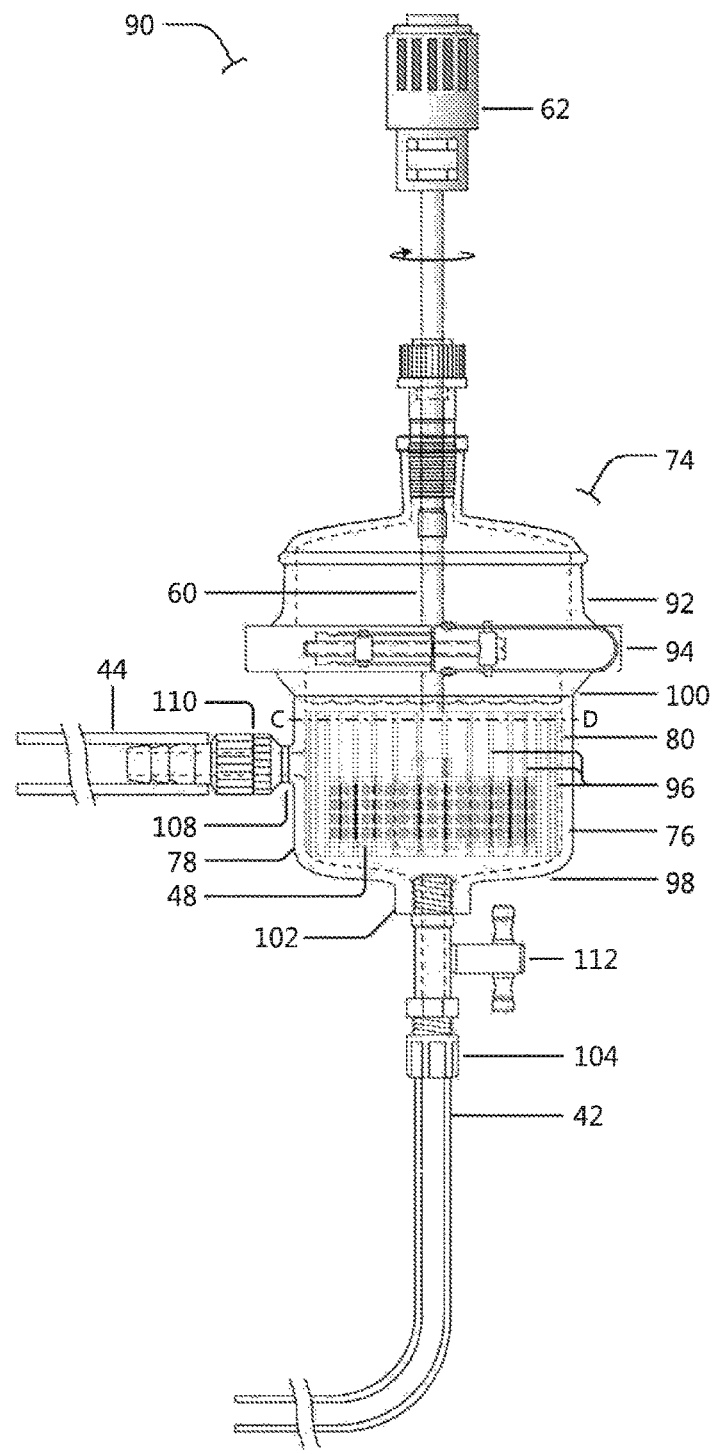
Figure 8:
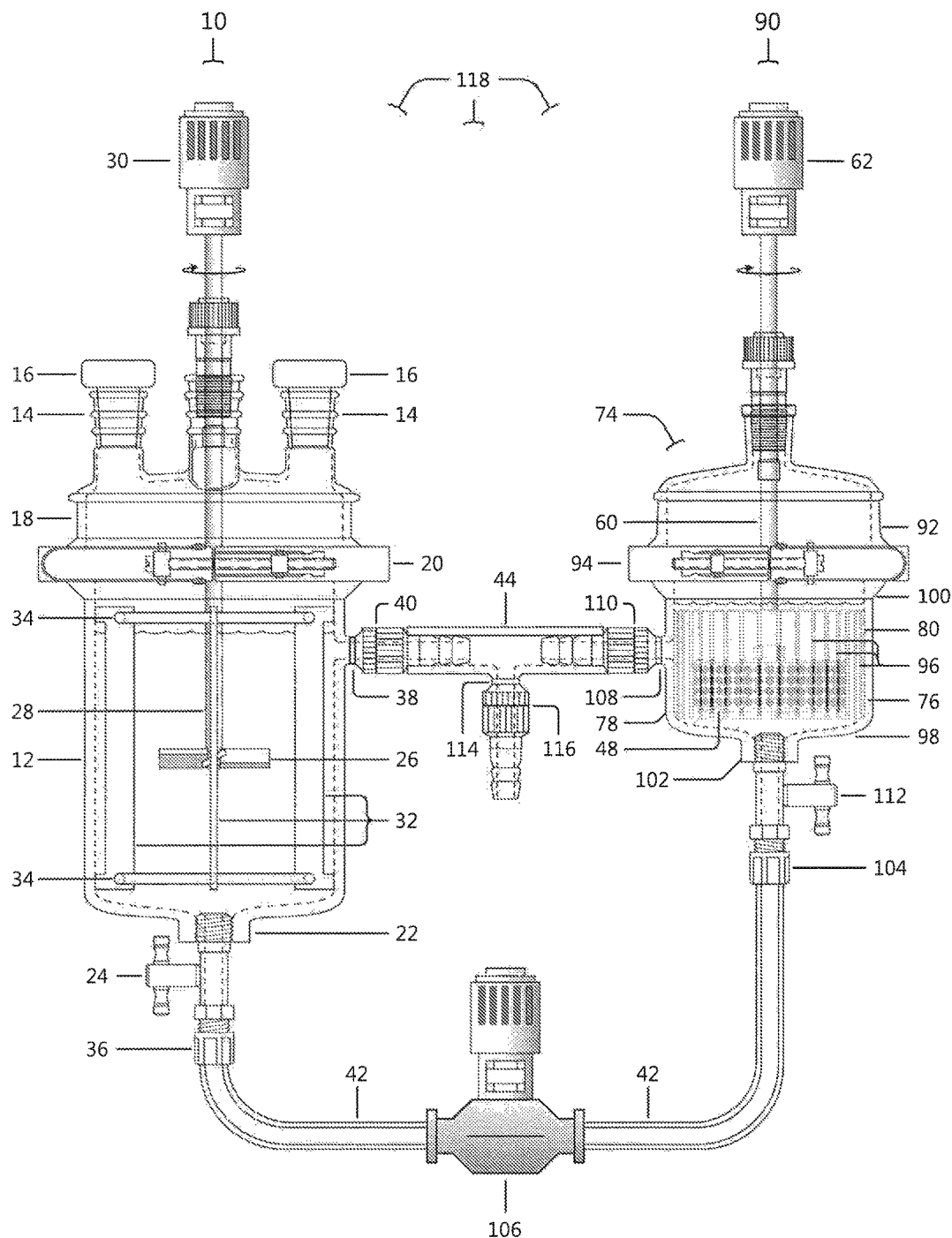

FIG. 6 presents horizontal cross-sections of reactors comprising a transformation device, with several examples of protrusions in the inner wall of the reactor that will result in working devices according to the invention;

FIG. 7 shows a side view of an auxiliary reactor comprising a transformation device as well as means for enhancing the fluidic shear stress in any of the two directions along said inner wall between said first end part and said second end part;

FIG. 8 describes a reactor arrangement comprising a main reactor and an auxiliary reactor; and FIG. 9 discloses simplified outlines of different additional reactor arrangements for batch or continuous processes.

DESCRIPTION OF PREFERRED EMBODIMENTS

FIG. 1 presents a side view of a reactor set-up 10 for performing a biological or chemical transformation, or physical or chemical trapping from, or release of agents to, a fluidic media by means of a solid reaction member. Such a reactor set-up is suitable as a main reactor in the reactor arrangement of the present application. A main reactor in accordance with the present application is a pilot scale or production scale multipurpose batch reactor. A suitable such reactor has a volume within the range of 1.0-1000 liters. The set-up 10 shown in FIG. 1 is comprised of a reactor vessel 12 having two inlet openings 14, with stoppers 16 fitted onto a lid 18 with closure means 20 as well as an outlet port 22 fitted with closure means 24. It also comprises an inlet port 38 that may be connected to an outlet connection of an auxiliary reactor. The outlet port 22 may be connected to an inlet connection of an auxiliary reactor. A typical way of connecting the main reactor is to add a pipe or a hose to the inlet port 38 as well as to the outlet port 22. The configuration of the lid is not limited to the description above. It could optionally be fitted with other inlets/outlets designed to accommodate the particular reaction being performed. The pipe or hose is then typically connected to a hose coupling or a pipe coupling. Such an arrangement is shown in FIG. 1. Accordingly, a connector 36 of the feed conduit 42 to an auxiliary reactor (shown in FIG. 7) has been connected to outlet port 22. Similarly, a connector 40 of a return conduit 44 from said auxiliary reactor (shown in FIG. 7) has been connected to an inlet port 38. The reactor vessel 12 as shown in FIG. 1 further comprises stirring means 26 powered by an electrically, pneumatically, or hydraulically driven motor 30 via a drive shaft 28. The exemplified reactor vessel 12 in FIG. 1 also comprises one or several voluminous baffles 32, which in the drawing are joined by two ring-shaped joining members 34, according to prior art.

FIG. 2 presents a side view of an embodiment of a transformation device 46 that constitutes an important part of an auxiliary reactor of the present application. The transformation device comprises a flow distributor 48 and a rotation and/or oscillation means 62, typically an electrically, pneumatically, or hydraulically driven motor, joined to the flow distributor 48 by a drive shaft 60. The flow distributor 48 has a first surface 50, a second surface 52 and a peripheral wall 54. The flow distributor 48 has an essentially cylindrical shape and the peripheral wall 54 has an essentially circular cross-section. There are fluid medium inlets 56 on the first 50 or on the second 52 surface, or optionally on both said surfaces. There are also fluid medium outlets 58 on the peripheral wall 54. The drive shaft 60 is mounted centrally on top of the first surface 50.

FIG. 3 shows a view of the first surface 50 of the flow distributor 48. There is optionally, or compulsory if there are no fluid inlets on the second surface 52 in FIG. 4, at least one fluid medium inlet 56 on the first surface 50 in close proximity to the attachment location of the drive shaft 60, or in other words adjacent to the intended axis of rotation of the second surface 52.

FIG. 4 shows a view of the second surface 52 of the flow distributor 48. There is optionally, or compulsory if there are no fluid inlets on the first surface 50 in FIG. 3, at least one fluid medium inlet 56 at, and/or adjacent to, the intended axis of rotation of the second surface 52.

FIG. 5 discloses a cross-sectional view from the first surface of an embodiment of the flow distributor 48 shown in FIG. 2 along the radial plane from A to B. In the shown embodiment, there is a plurality of confinements 64 separated from each other by separating walls 66. The confinements 64 may be fully or partially separated from each other. In the shown embodiment, there is a central fluid medium inlet 56 which is common to all confinements. In other embodiments comprising fully separated confinements there is at least one fluid medium inlet for each confinement. As already shown in FIG. 2, there are fluid medium outlets 58 arranged in the peripheral wall 54 in such a way that there is at least one such outlet 58 from each confinement 64. In the embodiment shown in FIG. 5 there is also a peripheral retaining mesh 68 along the inner surface of the peripheral wall 54. The peripheral retaining mesh 68 is permeable for the fluid reaction medium but not for the solid reaction members. In the shown embodiment, there is also, optionally and suspended on a mesh retainer 70, an inner retaining mesh 72, which also is permeable for the fluid reaction medium but not for the solid reaction members. In situations where the solid reaction member(s) are arranged in confinements 64 of the flow distributor right from the start, such an inner retaining mesh could be included in order to prevent the solid reaction members from escaping through the fluid medium inlet 56. However, in cases were solid reaction member(s) are added to and suspended in the fluid medium, such an inner retaining mesh should not be included as the solid reaction member(s) will be effectively drawn into the flow distributor 48 by its suction force and trapped therein when rotating/oscillating the flow distributor 48.

FIG. 6 presents a variety of possible horizontal cross-sections of a reactor 74 according to the invention along the radial plane from C to D in FIG. 7, comprising the flow distributor 48 of a transformation device housed in a reaction vessel with cylindrical outer surface 78, which inner surface 80 has been shaped to contain groves 82 (FIG. 6a) or protrusions 84 (FIG. 6b) of semi-elliptical shape, alternatively with rectangular 86 (FIG. 6c), or triangular 88 (FIG. 6d) protrusions of the inner wall, as a means of increasing the fluidic shear stress in the interstitial space between the flow distributor 48 and the inner wall 80 of the auxiliary reactor vessel 76. The distance V-V refers to the distance between the deepest points of two opposite groves (or valleys) and R-R to the distance between two opposite ridges. Typically, the distance R-R is 70-95% of the distance V-V. Typically, the number of groves/protrusions is 10-25. Based on these disclosures, the skilled person would be able to figure out numerous other protruding wall geometries that could equally well accomplish the task of increasing said fluidic shear stress.

FIG. 7 shows a side view of an auxiliary reactor 90 according to the present invention. The auxiliary reactor 90 comprises a cylindrical reaction vessel 74, having a first end part 98, a second end part 100, an outer wall 76 with an external outer surface 78 and an inner surface 80 between the first 98 and second 100 end parts. The auxiliary reactor 90 further comprises a transformation device (typically in accordance with what is disclosed in FIGS. 2-6) including a flow distributor 48, an electrically, pneumatically, or hydraulically driven means 62 for rotating and/or oscillating the flow distributor 48, connected to drive shaft 60, a lid 92 with closure means 94 which lid may have optional inlet/outlet openings and associated stoppers (not illustrated in the drawing). The shown embodiment of the auxiliary reactor also comprises a multitude of means 96 for enhancing the fluidic shear stress in any of the two directions along said inner wall between said first end part and said second end part, where the radial section C-D of the wall of the auxiliary reactor vessel is laid out with shear-inducing protrusions from the circular inner wall as exemplified by semispherical groves 82 and ridges 84, and rectangular 86 or triangular ridges 88, as illustrated by the top views shown in FIGS. 6a through 6d. The auxiliary reactor 90 also comprises an inlet port 102 with an inlet connection 104 located at the first 98 or second 100 end parts. In the shown embodiment, inlet port 102 is fitted with closure means 112 and located at the first end part 98. The auxiliary reactor 90 also comprises an outlet port 108 connected to a return conduit 44 by means of connector 110. Outlet port 108 is located in the wall 76 adjacent to, or slightly above, the flow distributor 48. A feed conduit 42 is adapted for being connected to an outlet of a main reactor and a return conduit 44 of an auxiliary reactor is adapted for being connected to an inlet of a main reactor.

FIG. 8 shows an example of a reactor arrangement 118 in accordance with the present application comprising a main reactor 10 and an auxiliary reactor 90 in accordance with the present invention. More specifically, the main reactor 10 (which may be of the same type as the reactor shown in FIG. 1) is connected to the auxiliary reactor 90 (which may be a reaction as shown in FIG. 7) by two different connections. The fluid connection supplying the auxiliary reactor starts at main reactor outlet port 22 which is connected to the inlet port 102 of the auxiliary reactor 90 by the feed conduit 42, by means of the main reactor outlet connector 36 and the auxiliary reactor inlet connection 104. The inlet port 102 of the auxiliary reactor is located directly below the flow distributor 48, whereby the fluidic medium transferred from the main reactor 10 is drawn directly into the fluid medium inlet(s) 56 and percolates the solid member(s) located in the confinements 64 (cf. FIG. 5). Similarly, the returning fluid contact starts at outlet port 108 of the auxiliary reactor from which return conduit 44 continues to connector 40 which is connected to the inlet port 38 of the main reactor (10), thus closing the fluidic loop.

The feed 42 and return 44 conduits are typically similar if not identical, but may, if space so requires, also be of different length and diameter, as in FIG. 8. Said conduits are typically hoses or pipes which are joined to the main reactor inlet 38 and outlet 22 ports in a suitable way. Examples of ways of joining the hoses or pipes are by screwing and/or clicking coupling mechanisms. It is of course also possible to join them permanently, for example by welding even though such a solution is less flexible. There are many different ways of joining hoses or pipes including welding, soldering, and mechanical coupling mechanisms, and the skilled person should be capable of selecting a suitable solution for a given situation. These connections may in some embodiments also be quite short and the main reactor connectors 36, 40 of the feed 42 or return 44 conduits may be located adjacent to the inlet 102 and/or outlet 108 ports of the auxiliary reactor, respectively.

By rotating or oscillating the flow distributor 48 of the auxiliary reactor, a flow of fluidic media is induced and maintained. Reactive centrifugal forces draw the fluidic media out from the flow distributor 48 by openings 58 in the peripheral wall 54 when the flow distributor is rotated (see FIG. 2). Accordingly the pressure inside the flow distributor is reduced and fluidic media is drawn into the flow distributor through one or more inlets 56 of the first and/or second surface of the flow distributor. In the shown embodiment, the inlet 56 of the flow distributor 48 is facing the inlet port 102 of the auxiliary reactor 90. Fluidic media is drawn from the inlet port 102 into inlet(s) 56 and exits through outlet port 108 into return conduit 44 when the flow distributor 48 is rotated or oscillated. Accordingly, a rotating or oscillating flow distributor may act as a pump and induce, as well as maintain, a circulation from the main reactor 10 through its outlet port 22, into the inlet port 102 of auxiliary reactor 90, and back again to main reactor 10 through the auxiliary reactor 90 outlet port 108 via the return conduit 44 into the inlet port 38 of the main reactor 10. In some embodiments, this circulation may be further amplified by an additional pumping arrangement 106 fitted in-line with the feed conduit 42 (as shown in FIG. 8) and/or or the return conduit 44.

The main reactor 10 of the reactor arrangement 118 shown in FIG. 8 furthermore comprises stirring means 26 which is powered by motor 30. The main reactor 10 could also comprise several baffles 32. The shown embodiment also comprises ports for auxiliary equipment for reagent addition, condensation, sources of vacuum or pressure, measurement devices, etc. arranged at one or more outlets 14 of the reactor, for example a cooler used to reflux solvents. Another useful piece of auxiliary equipment connected to outlet 14 could be a device designed to trap by-products that may be formed in reactions run in the reactor. Examples of such by-products are water and acetone.

The reactor arrangement depicted in FIG. 8 may also be used in continuous processes. In that case, a flow of incoming fluidic media is forwarded in a suitable conduit (not shown in FIG. 8) connected to one of the outlets 14 of the main reactor 10. In this embodiment, the return conduit 44 comprises a product outlet port 114 and an associated product outlet connection 116 where an outgoing conduit (not shown in FIG. 8) adapted for leading away product-containing outgoing fluidic media could be connected. Several embodiments can be considered for continuous processes. In some embodiments of the invention, a part of the fluidic media in the return conduit 44 is lead to the outlet port 114 and the outgoing conduit (not shown) while the remaining part of the fluidic media is returned to the main reactor 10. In some embodiments, all of the fluidic media in the return conduit 44 is forwarded to the outgoing conduit (not shown) and nothing is returned to the main reactor 10.

Reactor arrangements in accordance with further embodiments of the present invention are outlined in FIG. 9a-FIG. 9f. The embodiment shown in FIG. 9a is a reactor arrangement for a batch process where fluidic media is circulated from the main reactor 10 through two auxiliary reactors 90a, 90b connected in series and back again to the main reactor. The embodiment shown in FIG. 9b is also a reactor arrangement for a batch process. In this embodiment, the fluidic media is circulated from the main reactor 10 through two auxiliary reactors 90a, 90b connected in parallel.

The reactor arrangements of FIG. 9c-9f all relate to continuous processes. The embodiment shown in FIG. 9c is a continuous reactor arrangement where incoming fluidic media is fed into a main reactor 10 and then forwarded through two auxiliary reactors 90a, 90b connected in series. The flow of fluidic media from the last auxiliary reactor 90b is forwarded to downstream processing (not shown). The embodiment shown in FIG. 9d is a reactor arrangement in accordance with what is disclosed in detail regarding FIG. 8. Incoming fluidic media is fed into a main reactor 10. Fluidic media is forwarded from the main reactor through auxiliary reactor 90. A part of the outgoing flow from the auxiliary reactor 90 is forwarded to downstream processing and the rest is returned to main reactor 10. The embodiment shown in FIG. 9e is similar to the embodiment of FIG. 9d, but here the whole outgoing flow from the auxiliary reactor 90 is forwarded to downstream processing. The embodiment shown in FIG. 9f is also similar to the embodiment of FIG. 9d, but here the flow of fluidic media to downstream processing is lead through an additional auxiliary reactor 90b. The skilled person realizes that additional similar reactor arrangements comprising a plurality of auxiliary reactors are possible.

A reactor arrangement according to the present application is associated with several advantages. Although a transformation device comprising a flow distributor and a motor provides excellent results, the assembling and de-assembling in a reactor in association with maintenance and cleaning could be complicated and time consuming. Furthermore, the complexity and time consumption increases for larger reactors. However, in accordance with the teachings of the present application, the transformation device could be arranged in a much smaller auxiliary reactor which is much easier to assemble and de-assemble.

A consequence of the reactor arrangement of the present application is that the main reactor has a more passive role compared to the auxiliary reactor. On the other hand, it is possible to use the reactor arrangement in several quite different ways. In one embodiment a reaction catalyzed by a solid phase catalyst is run in the reactor arrangement. In this situation, the solid phase catalyst is located in the flow distributor in the auxiliary reactor. The solid phase catalyst may be arranged in the flow distributor at the onset of the reaction or it may be added as a suspension to the fluidic media and later collected in the flow distributor in accordance with what is disclosed in SE 1351168-8.

The reactor arrangement could also be used for reactions where solid particles are formed and where all other components are either dissolved or in a liquid state. In such a case, the solid particles are collected in the flow distributor in accordance with what is disclosed in SE 1351168-8. Another possibility is to use a catalyst that is soluble at the reaction temperature but that is not soluble at lower temperatures. In this case, it is possible to chill the reaction mixture when the reaction is completed in order to obtain precipitated catalyst particles. These particles may then be collected in the flow distributor in accordance with what is disclosed in SE 1351168-8.

Reactions which may be suitable for a reactor arrangement in accordance with the present application are solid-phase organic synthesis wherein a precursor molecule is bound on a solid member and synthesis is carried out from this precursor in step-by-step fashion by successive addition of reactant/activation/coupling solutions followed by a final decoupling step, according to prior art. Examples of such reactions are solid phase synthesis of peptides and oligonucleotides. Other suitable schemes are reactions involving a solid phase catalyst which is not consumed. A nonexhaustive list of such reactions are metal-catalyzed hydrogenations of carbon-carbon multiple bonds, C=O bonds, N-containing multiple bonds, reductive amination, hydrogenolytic reactions such as breaking of C—O and CN bonds, and hydrogenolysis of C—C, C—S, C—Se, C-Halogen, C—Si, N—O, N—N, and Si—O bonds, coupling reactions, bond-breaking reactions such as decarbonylation, dehydration, dehydrogenation, or breaking of S—H Bonds, oxidations with molecular oxygen or ozone as gaseous reagents, or hydrogen peroxide as liquid oxygen precursor, condensation reactions (with immobilized acids or bases as catalysts) and various asymmetric catalytic schemes (Heitbaum, et al., *Angew. Chem. Int. Ed.* 2006, 45, 4732; K. Ding, Y. Uozumi (Eds.), "*Handbook of Asymmetric Heterogeneous Catalysis*", Wiley, 2008). Background of heterogeneous catalytic chemical schemes suitable for use in the transformation device is outlined in monographies such as G. V. Smith and F. Notheisz, "*Heterogeneous Catalysis in Organic Chemistry*", Academic Press, 1999; R. A: Sheldon, H. van Bekkum, "*Fine Chemicals through Heterogeneous Catalysis*", Wiley, 2001; S. Nishimura, "*Handbook of Heterogeneous Catalytic Hydrogenation for Organic Synthesis*", Wiley, 2001; A. Kirschning (Ed.), "*Immobilized Catalysts—Solid Phases, Immobilization and Applications*" (Topics in Current Chemistry, Vol. 242), Springer, 2004; R. A. van Santen, M. Neurock, "*Molecular Heterogeneous Catalysis*", Wiley, 2006; N. Mizuno, "*Modern Heterogeneous Oxidation Catalysis—Design, Reactions and Characterization*", Wiley, 2009; R. H. Crabtree (Ed.), "*Handbook of Green Chemistry, Volume 2: Heterogeneous Catalysis*", Wiley, 2009; and P. Barbaro and F. Liguori, "*Heterogenized Homogeneous Catalysts for Fine Chemicals Production—Materials and Processes*", Springer, 2010. Suitable procedures involving enzymatic reactions and biotransformations involving whole cells are, e.g., found in G. F. Bickerstaff, "*Immobilization of Enzymes and Cells*", Humana Press, Totowa, N.J., 1997; A. S. Bommarius, B, R. Riebel, "*Biocatalysis*", Wiley-VCH, 2004; W.-D. Fessner, T. Anthonsen, "*Modern Biocatalysis-Stereoselective and Environmentally Friendly Reactions*", Wiley-VCH, 2009; P. T. Anastas (Ed.), "*Handbook of Green Chemistry, Volume 3—Biocatalysis*", Wiley-VCH, 2009; J. Whittall, P. W. Sutton (Eds.), "*Practical Methods for Biocatalysis and Biotransformations*", Wiley, 2010.

The reaction arrangement may be fitted with means for shifting the equilibrium of reactions run therein in an advantageous way. Typically, this is done by removing a product of the reaction. This can be done by selective adsorption, extraction, continuous filtration, and continuous carbon treatment of a product or a by-product.

The person skilled in the art realizes that the present invention by no means is limited to the preferred embodiments described above. On the contrary, many modifications and variations are possible within the scope of the appended claims.

Additionally, variations to the disclosed embodiments can be understood and effected by the skilled person in practicing the claimed invention, from a study of the figures, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combinations of these measures cannot be used to advantage.

The invention claimed is:

1. An auxiliary reactor for performing, by means of at least one solid reaction member(s), a biological or chemical transformation, or physical or chemical trapping from or release of agents to a fluidic media, said auxiliary reactor being adapted for being connected to a main reactor, said auxiliary reactor comprising:
   a cylindrical reaction vessel having:
      a first end part,
      a second end part, and
      an outer wall comprising an outer surface and an inner surface between the first end part and the second end part;
   a transformation device mounted in said auxiliary reactor, the transformation device comprising:
      a flow distributor having an essentially cylindrical shape, a first essentially flat surface, a second essentially flat surface, and a peripheral wall having an essentially circular cross-section,
      at least one fluid medium inlet located in vicinity of the center of said first and/or second surface, said inlet being adapted for receiving fluid medium and optionally being adapted for receiving initially suspended solid reaction members,
      at least one fluid medium outlet permeable for said fluid medium but impermeable for solid reaction members, said outlet(s) being located on said peripheral wall,
      a driving shaft located on said first surface for enabling rotation or oscillation of the flow distributor, and at least one confinement wherein said solid reaction member(s) can be trapped and said transformation is performed; and a means for rotating and/or oscillating the device using the driving shaft;

characterized in that said auxiliary reactor further comprises:

a) a feed conduit adapted for being connected to an outlet port of said main reactor; and b) a return conduit adapted for being connected to an inlet port of said main reactor.

2. The auxiliary reactor according to claim 1, characterized in that an inlet port of said auxiliary reactor connected to said feed conduit is located at the first end part or the second end part, and in that an outlet port of said auxiliary reactor connected to said return conduit is located in said outer wall adjacent to the flow distributor.

3. The auxiliary reactor according to claim 1 characterized in that it further comprises a pump adapted to enhance the flow of a liquid reaction medium from said main reactor through said feed conduit, transformation device, cylindrical reactor vessel, and return conduit back to said main reactor, thereby assisting the inherent pumping action of the transformation device.

4. The auxiliary reactor according to claim 1, characterized in that said inner surface of the cylindrical reactor vessel comprises means for enhancing the fluidic shear stress in any of the two rotary directions along said inner surface between said first end part and said second end part.

5. The auxiliary reactor according to claim 4, characterized in that said means for enhancing the fluidic shear stress consisting of at least one indentation in said inner wall shaped as (a) semi-elliptically-shaped grove(s) or protrusion(s) of semi-elliptical, rectangular or triangular shape, each indentation extending in a direction from said first end part to said second end part.

6. The auxiliary reactor according to claim 4, characterized in that the reactor comprises 2-30 of said means for enhancing the fluidic shear stress.

7. A reactor arrangement for performing, by means of at least one solid reaction member, a biological or chemical transformation, or physical or chemical trapping from, or release of agents to, a fluidic media in a continuous process or in a batch process, wherein said reactor arrangement comprises:

the main reactor; and at least one of the auxiliary reactor according to claim 1, wherein the inlet port of the auxiliary reactor is connected to an outlet port of the main reactor.

8. The reactor arrangement according to claim 7 wherein the outlet port of one of the at least one auxiliary reactor is connected to an inlet port of the main reactor.

9. The reactor arrangement according to claim 7, wherein the reactor arrangement is adapted for forwarding at least 0-100% of the outgoing flow of fluidic media from an auxiliary reactor of the arrangement to downstream processing and returning the rest of the flow to the main reactor.

10. The reactor arrangement according to claim 7, characterized in that said main reactor further comprises a stirring means and a plurality of baffles for mixing said fluidic media.

11. The reactor arrangement according to claim 7, characterized in that the main reactor further comprises one or more outlet opening(s) which may optionally be fitted with an auxiliary means for exchange or state transformation (for instance condensation or freezing) of matter, or for measurement probes.

12. A method for performing, by means of at least one solid reaction member(s), a biological or chemical transformation, or physical or chemical trapping from, or release of agents to, a fluidic media, comprising the steps of:

a) providing the reactor arrangement according to claim 8;

b) adding at least one solid reaction member to a confinement of said flow distributor;

c) adding the fluidic media to the main reactor and the auxiliary reactor of the reactor arrangement; and d) activating the means for rotating and/or oscillating the device;

whereby the biological or chemical transformation, or physical or chemical trapping from, or release of agents to, the fluidic media is initiated.

13. The method for performing a chemical or biological transformation in accordance with claim 12, wherein the method comprises the step of continuous removal a product or by-product formed during the transformation by a step selected from the group of distillation, extraction, filtration and adsorption.

14. The method for performing a physical or chemical trapping in accordance with claim 12, wherein the method comprises the step of trapping solid particles that are suspended in the fluidic media.

15. The method for performing physical trapping in accordance with claim 12, wherein the fluidic media is an aqueous media containing specific radioactive ions and the flow distributor comprises an ion exchanger capable of adsorbing said specific radioactive ions.

* * * * *